United States Patent [19]

Mueller et al.

[11] Patent Number: 4,864,066

[45] Date of Patent: Sep. 5, 1989

[54] PREPARATION OF ALKANEDIOLS FROM ALKYNOLS

[75] Inventors: Herbert Mueller; Herbert Toussaint, both of Frankenthal; Juergen Schossig, Fussgoenheim, all of Fed. Rep. of Germany

[73] Assignee: BASF Aktiengesellschaft, Ludwigshafen, Fed. Rep. of Germany

[21] Appl. No.: 189,298

[22] Filed: May 2, 1988

[30] Foreign Application Priority Data

May 23, 1987 [DE] Fed. Rep. of Germany ....... 3717405
Oct. 16, 1987 [DE] Fed. Rep. of Germany ....... 3735108

[51] Int. Cl.$^4$ ........................ C07C 29/17; C07C 31/20
[52] U.S. Cl. .................................................... 568/861
[58] Field of Search ......................................... 568/861

[56] References Cited

U.S. PATENT DOCUMENTS

| | | | |
|---|---|---|---|
| 2,953,605 | 9/1960 | Hort | 508/861 |
| 2,967,893 | 1/1961 | Hort et al. | 568/861 |
| 3,184,513 | 5/1965 | Moore et al. | 508/861 |
| 3,449,445 | 6/1969 | Wetherill | 260/635 |
| 3,759,845 | 9/1973 | Rudoff | 252/466 J |
| 4,026,960 | 5/1977 | Nishida et al. | 508/861 |
| 4,048,116 | 9/1977 | Voges et al. | 252/470 |
| 4,153,578 | 5/1979 | De Thomas | 252/438 |
| 4,180,687 | 12/1979 | Burrus | 568/856 |
| 4,213,000 | 7/1980 | Coates | 568/861 |
| 4,371,723 | 2/1983 | Chiddix | 568/856 |

FOREIGN PATENT DOCUMENTS

| | | | |
|---|---|---|---|
| 2004611 | 2/1972 | Fed. Rep. of Germany . | |
| 2145297 | 3/1972 | Fed. Rep. of Germany . | |
| 2536273 | 2/1977 | Fed. Rep. of Germany . | |
| 694954 | 11/1953 | United Kingdom | 568/861 |
| 788969 | 1/1958 | United Kingdom | 568/861 |
| 1242358 | 8/1971 | United Kingdom . | |

*Primary Examiner*—J. E. Evans
*Attorney, Agent, or Firm*—John H. Shurtleff

[57] ABSTRACT

A process for the preparation of alkanediols by hydrogenation of alkynediols of from 3 to 8 carbon atoms in which a solution of the alkynediol in an alcohol of from 1 to 8 carbon atoms, the mass fraction of alkynediol being more than 5%, of water at most 10%, and of alkanediol from 20% to 85%, is hydrogenated at temperatures of 110° C. to 240° C. and pressures greater than 10 bar, the pH being greater than 6.

6 Claims, No Drawings

PREPARATION OF ALKANEDIOLS FROM ALKYNOLS

The present invention relates to a process for the preparation of alkanols by catalytic hydrogenation of alkynols.

It is known that alkanols such as propanol or 1,4-butanediol can be prepared by catalytic hydrogenation of alkynols such as 2-propyn-1-ol or 2-butyne-1,4-diol. In the processes described in German Laid-Open Application No. 25 36 273 or U.S. Pat. No. 4,153,578 nickel or cobalt catalysts, either as Raney metals or as composite catalysts, are used. Supported catalysts containing nickel together with copper, aluminum, and manganese have been proposed for the hydrogenation of acetylenic alcohols (cf. German Laid-Open Application No. 21 45 297, U.S. Pat. No. 3,449,445, and German Laid-Open Application No. 20 04 611).

The catalyst described in German Laid-Open Application No. 25 36 373 that contains nickel together with copper, manganese, and molybdenum gives satisfactory on-stream times in the hydrogenation of 2-butyne-1,4-diol to 1,4-butanediol, but comparatively high hydrogen pressures and temperatures must be chosen if the purity of the butanediol is to satisfy stringent requirements. Only in this way is it possible to remove carbonyl compounds and their derivatives, which have detrimental effects in many applications, by reduction to such an extent that their harmful influence can be tolerated. However, increasing the severity of the reaction conditions in this way promotes the formation of butanol, which is undesirable, and reduces the yield; at the same time it increases formation of the undesirable side product 2-methylbutanediol (cf. U.S. Pat. No. 4,153,578). And finally, it is difficult to prepare the catalyst containing active metals reproducibly, with always the same activity and effective life.

Catalysts containing nickel and cobalt are preferred for the industrial hydrogenation of alkynols. Since it is recognized that both nickel and cobalt dusts are carcinogenic substances, it is both difficult and expensive to work with fixed-bed catalysts containing nickel or cobalt. Nowadays the employment of such catalysts can only be justified if the bed retains its original utility (e.g. with respect to activity, selectively, and strength) for very long periods and the catalyst does not have to be replaced frequently. For this reason the use of suspended nickel catalysts, which largely avoids these difficulties, has already been proposed (U.S. Pat. No. 4,599,466).

The hydrogenation of 2-butyne-1,4-diol to 1,4-butanediol is particularly important industrially. For this the crude aqueous solutions of butynediol obtained by the Reppe synthesis of butynediol from acetylene and formaldehyde are employed (cf. U.S. Pat. No. 4,371,723).

Removal of carbonyl compounds and their acetals has proved an especially difficult problem in the hydrogenation of these crude aqueous solutions of butynediol. Because of the process by which they are prepared, these solutions contain concentrations of formaldehyde that cannot be neglected, since formaldehyde interferes with the hydrogenation of butynediol and leads to the formation of undesirable side products. For this reason it has already been suggested that the formaldehyde should be removed before hydrogenation of crude butynediol solutions, by distillation (U.S. Pat. No. 3,449,445 column 2, lines 57–60) or by formation of harmless polymer in the presence of alkali (U.S. Pat. No. 4,180,687).

Formaldehyde not only has deleterious effects on the action of the hydrogenation catalyst: with butynediol it forms 2-methyl-butane-1,4-diol during hydrogenation. This compound is an undesirable impurity in butanediol, because it is the source of impurities that are scarcely separable in products made from butanediol, such as N-methylpyrrolidone. It is also practically impossible to separate from 1,4-butanediol by distillation. For this reason it is proposed in U.S. Pat. No. 4,153,578 that the solution of butynediol should be at first hydrogenated as far as possible at low temperatures and pressures, then completely hydrogenated in a second stage over a special Raney nickel catalyst containing molybdenum. In this way it is possible to reduce the methylbutanediol content of the butanediol from the normal values of from 1.5% to 2% to at best from 0.3% to 0.5%. Such a process however is elaborate and expensive.

The butynediol solutions described contain more than 0.2% poly(oxymethylenes) as well as free formaldehyde. These can coat the active surface of the catalyst and thus impair hydrogenation. They also appear as a valueless residue when the pure butanediol is distilled off, and its disposal adds to the cost of purifying the crude butanediol solution. it has been found too that lower poly(oxymethylenes) can be found in the distilled butanediol if the distillation treatment is not carried out with a very great deal of technical elaboration. Butanediol containing impurity of this kind is unsuitable for the preparation of, for instance, tetrahydrofuran (THF), since poly(oxymethylene) reduces the activity of the dehydration catalysts. THF is a very important product made from 1,4-butanediol, much of which is used for the preparation of polytetrahydrofuran. For this purpose the THF must be very pure, since impurities affect the attainable molecular weights of the polymers, the rate of polymerization, the activity and effective lives of the polymerization catalysts, and particularly the color of the polymer. It has been suggested that THF should be treated with alkali solutions before it is polymerized, to suppress discoloration of the polymer (U.S. Pat. No. 4,544,774).

For these reasons there was a need to find a process for the hydrogenation of alkynols such as 2-butyne-1,4-diol that would make it possible to obtain an intermediate particularly well suited for the preparation of THF. The hydrogenation of butynediol should proceed especially economically, with a high rate of throughput and low catalyst costs. The butanediol should have the required purity and be produced in high yield. It was desirable also that the hydrogenation process should convert side products in crude 2-butyne-1,4-diol, such as hydroxybutyraldehyde and its acetals and acetals formed with butynediol, to 1,4-butanediol as well. Further, it should be sought to degrade the formaldehyde polymers - poly(oxymethylenes) - present in the crude alkynediol solutions by hydrogenation and convert them to methanol. This would give valuable methanol from the otherwise worthless polymers, and at the same time relieve the final distillation of the pure butanediol.

These problems have already been solved in part by the process described in U.S. Pat. No. 4,599,466, where the crude aqueous solutions of butynediol are hydrogenated at temperatures above 190° C. after addition of nickel salts of organic acids. The catalysts formed thereby are at first extraordinarily selective, cause the formation of only small amounts of side products, and give high yields. However, after long periods of production these good properties fall off. At first there is little impairment of selectivity, but it increases as time goes on.

In the novel process, which very largely fullfills the tasks imposed and avoids the drawbacks mentioned, alkynediols of from 3 to 8 carbon atoms are hydrogenated catalytically at high temperatures and pressures by hydrogenating a solution of the alkynediol in an alkanol of from 1 to 8 carbon atoms, in which the mass fraction of alkynediol is greater than 5%, of water at most 10%, and of alkanol from 20% to 85%, at temperatures of from 110° C. to 240° C. under pressures greater than 10 bar, the pH being greater than 6.

Alkynediols suitable for the novel hydrogenation process are those with from 3 to 8 carbon atoms. Examples are 2-butyne-1,4-diol, 3-hexyne-2,5-diol, and 2,5-dimethyl-3-hexyne-2,5-diol. Hydrogenation of 2-butyne-1,4-diol to 1,4-butanediol is of special interest industrially.

The alkynediols specified are hydrogenated in solution in an alkanol of from 1 to 8 carbon atoms. The mass fraction of alkynol in the starting solution is greater than 5%, for instance from 10% to 80%, and preferably from 30% to 70%. The mass fraction of water in the starting solution is at most 10%, and preferably it is less than 5%. The mass fraction of alkanol in the starting solution is from 20% to 85%, and preferably from 30% to 70%. The alkanol of the kind specified may have one or two hydroxyl groups, but monohydric unbranched or branched alkanols of from 1 to 5 carbon atoms are preferred, for example methanol, ethanol, propanol, butanol, or 2-methyl-2-propanol; of these, methanol has special preference. Glycols such as ethylene glycol or 1,4-butanediol are also suitable solvents for the novel process, but because of their high boiling points they do not deserve preference.

The alcoholic starting mixtures can also contain the impurities arising from the synthesis of the alkynediol. The mass fraction of such impurities may be up to 4%, for instance; examples of the impurities themselves are aldehydes such as formaldehyde and its polymers, acetals, nonvolatile or hardly volatile acetylenic compounds, and alkali salts of lower carboxylic acids such as formic and acetic acids. The impurities may also include silica and alkali or alkaline earth silicates, originating in the catalyst for the ethynylation, and formates, derived from formaldehyde by the Cannizzaro reaction. If the pH was buffered in the ethynylation process compounds such as sodium acetate also remain.

The mixtures required for the novel process, which consists mainly of alcoholic solutions of alkynediols, are typically derived from the crude aqueous solutions of 2-butyne-1,4-diol that are formed by the known synthesis from acetylene and aqueous formaldehyde, which is practised industrially on a large scale - see *Ullmanns Enzyklopädie der Technischen Chemie*, vol. III, pp. 109–119, and vol. IV, pp. 754–757 (1953), German Published Application No. 24 21 407, German Laid-Open Application No. 25 36 273. Water is first removed by evaporation, leaving a mass fraction of at most 10% and preferably not more than 5%. The rest is then distilled off at atmospheric or reduced pressure. The concentrate, which can contain the impurities boiling at higher temperatures than water, such as carbonyl compounds and their acetals, higher alkynols, and formaldehyde polymers, and the nonvolatile residues mentioned above, is then taken up in an alkanol, enough of which is taken to give the starting solutions described above.

A starting solution that is particularly suitable for the preparation of 1,4-butanediol contains, for instance, the following components in the mass fractions stated: from 30% to 70% 2-butyne-1,4-diol, from 30% to 70% methanol, from 0.2% to 5% water, and from 0.2% to 5% impurities arising from the previous synthesis, such as formaldehyde, poly(oxymethylene) acetals, nonvolatile organic substances, sodium formate, and 2-propyn-1-ol. Usually such a starting solution is so alkaline that its pH value is greater than 6.

The preferred pH value is from 7 to 9. If the pH is more than 10 it is advisable to reduce it by addition of a buffer. The pH is measured after addition of an equal weight of water, by means of a glass electrode for instance.

All the catalysts usually employed for hydrogenation are suitable, such as platinum, palladium, ruthenium, nickel, cobalt or copper. The hydrogenation catalysts may also contain several of these metals that act catalytically. The preferred catalysts are those whose catalytic component consists of more than 50% nickel - preferably more than 99% - in the form of Raney nickel or nickel formed by the decomposition of nickel(O) complexes or nickel formate. The nickel catalysts may contain proportions of other metals that promote hydrogenation, such as palladium, rhodium, ruthenium, cobalt or copper, but pure nickel catalysts are preferred.

In a preferred embodiment of the process the catalyst is introduced to the alcoholic solution of the alkynediol to be hydrogenated as the nickel salt of a carboxylic acid of two or more carbon atoms. In the simplest case nickel acetate is employed, enough to make the mass fraction of nickel from 0.005% to 0.05% for instance, or more especially from 0.01% to 0.03%. Under the conditions of the reaction the catalytically active nickel is formed in the reaction medium automatically. It does no harm to the reaction if higher concentrations of nickel are used, but then the process is less economical. Suitable nickel salts, which are sufficiently soluble in the alcoholic solutions of the alkynols, include, for example, nickel acetate, nickel formate, nickel butyrate, and nickel 2-ethylhexanoate.

It is also possible to use supported catalysts, the active metal being applied to one of the usual support materials. The catalysts are then often employed as suspensions, in stirred reactors or bubble columns for instance, because this is advantageous for temperature control. The catalysts can however be arranged in a fixed bed, through which the substrate to be hydrogenated passes in the ascending-flow or trickle methods, of which the ascending-flow method is preferred.

It has been found that when catalysts such as those supported on alumina or silica are employed in the novel process they have an effective life of a year or more before they lose activity and strength. This is surprising, since such supported catalysts used in hydrogenation processes common in industry are rapidly destroyed by alkynol solutions and last for only one to three months.

It is advantageous to employ fixed-bed catalysts, because no separation from the reaction product is necessary. Nevertheless, suspended catalysts are often preferred, since it is very easy to separate them from the product of the reaction - by filtration through porous sintered material or magnetically, for instance - , especially when they are nickel catalysts. The procedure in which organic nickel salts are used as precursors of the catalysts has the advantage that the concentrations of active metal employed are very low, and the filters can be cleaned very simply by dissolving the metal in acid; the metal salts are returned to the hydrogenation reaction. Since the operations are carried out with moist metal in a closed system there is no hazard to plant operators.

The starting mixture is hydrogenated in the presence of hydrogenation catalysts at temperatures of form 110° C. to 240° C., preferably at 110° C. to 210° C. If the catalyst is introduced to the alkynediol solution as the metal salt of an organic acid the hydrogenation is carried out at temperatures over 150° C., most advantageously at from 170° C. to 240° C. The partial pressure of the hydrogen should be between 10 bar and 350 bar for the hydrogenation; pressures between 50 bar and 250 bar, especially between 150 bar and 250 bar, are preferable. If higher pressures are used then those preferred there is not considerable advantage in view of the added cost.

In this manner it is possible to prepare, in a single stage, butanediol of the highest purity with quantitative selectivity at temperatures of about 200° C. and a total pressure of 250 bar from a 50% solution of butynediol in methanol to which has been added 0.04% nickel as nickel acetate. The catalyst concentration depends on the temperature chosen and the required velocity. If it is between 0.01% and 0.1% (cf. the even lower figures given above) it is much lower than in the other hydrogenation processes employed.

The novel process can be carried out batchwise or continuously. In the continuous process, which is particularly advantageous, and can be carried out in a stirred reactor or a recirculation reactor, for example, the heat of hydrogenation is used to advantage to bring the temperature of the fresh inflow to, say, between 90° C. and 180° C. before it enters the reactor. Heating can be carried out in an external heat exchanger, for example, through which some of the reaction mixture is circulated. As the hydrogenation progresses along the reaction zone the temperature of the reaction mixture rises to, say, 120° C. or more. The final temperature depends in this case mainly on the rate of inflow of fresh material and, for example, the rate at which heat is abstracted for steam generation.

If hydrogenation is not carried out continuously the semicontinuous process is recommended. The catalyst is suspends or dissolved in a small portion of hydrogenated reaction mixture, which is brought into the reaction vessel. Butynediol solution is then introduced at the reaction temperature and pressure, the rate of inflow being adjusted to the rate of hydrogenation. In this way there is never too much butynediol in the vessel at once.

The catalyst metal suspended in the reaction mixture is removed after hydrogenation by usual physical methods of separation, such as centrifugation, sedimentation, or filtration. The catalysts can be returned to the reaction; they retain their original activity over very long periods of use. If the catalyst is introduced as an organic nickel salt, and is automatically activated under the conditions of the reaction, the nickel concentration required is so low that it is not worthwhile to isolate the metal to recover it; in this case the metal separated is best dissolved in an organic acid and the salt introduced into fresh inflow for hydrogenation.

The alkanediols obtained from alkynols by the novel process are extraordinarily pure; selectivity is practically complete. Thus, for instance, butanediol prepared by the novel process is free from carbonyl compounds or traces of compounds with olefinic unsaturation. Its platinum-cobalt color is well below 50. The mass fraction of methylbutanediol even in the crude product is less than 0.1%, and less than 0.05% is preferred. The fraction of nonvolatile residues in the crude butanediol solution is at most 40% of that of the crude butynediol solution used for hydrogenation. Because of its great purity the butanediol obtained is particularly suitable for the preparation of THF intended, say, for the manufacture of polytetrahydrofuran of low color.

The long life of the catalysts makes it possible to carry out the process with very good results with a fixed catalyst bed, either by the ascending-flow or trickle methods, without feat of having to replace the catalyst frequently because of decline in activity. The process is notably economic because the reactors can be run for practically unlimited periods and do not need to be subjected to cleaning operations. Since the hydrogenation can be carried out at temperatures of over 180° C., the enthalpy of hydrogenation given up during the reaction can be recovered at a high temperature level, which further improves the economics of the process. The rate of output per unit of reactor volume reaches values very much higher than those for known processes operated at the same temperature and pressure.

It is surprising that high yields are obtained without previous separation of impurities from the crude solutions, since other solvents with properties comparable to those of the alcohols used in the novel process, such as tetrahydrofuran or diethyl ether, do not display the effect of increasing the yield of hydrogenation observed here. It would have been expected that carbonyl groups might form by dehydration of alcohols - present in very high concentrations, because of their use as solvent - and take part in undesirable side reactions, such as condensation or acetal formation. It could also not be foreseen that the polymeric alkynols present in the starting solutions, whose deleterious effect on hydrogenation is recognized, and whose exact structure is not known, would be transformed into the required alkanediols in the novel hydrogenation process, and thus bring the final yield based on the amount of alkynediol to more than 100%.

EXAMPLE 1

A crude solution of 2-butyne-1,4-diol obtained by the reaction of acetylene with formaldehyde in aqueous solution was taken as the starting material for the continuous hydrogenation of butynediol. It consisted of from 1% to 2% methanol, from 1% to 2% propynol, 0.9% formaldehyde, 0.6% formaldehyde polymers. 39% 2-butyne-1,4-diol, from 55% to 60% water, and from 2% to 4% unidentified acetals and nonvolatile substances.

This solution was freed from the bulk of the water by means of a rotary film evaporator operated at a temperature of from 140° C. to 150° C. under atmospheric pressure. The hot residue was then evaporated under a pressure of from 20 mbar to 30 mbar until the water content was from 0.3% to 0.85. Nearly all the methanol, formaldehyde, and propynol in the butynediol solution was driven off with the water. The substance was dissolved in its own weight of methanol, giving a methanolic solution of the following composition: 475 2-butyne- 1,4-diol, 0.3% water, 50% methanol, 0.15% formaldehyde, and 2.5% other side products or impurities.

Nickel acetate was added to the methanolic solution of butynediol in sufficient quantity to make the mass fraction of nickel in the solution 0.05%. The pH of the methanolic solution of butynediol and nickel acetate was adjusted to the range favorable for the process, from 8 to 9, by the addition of 3 ml of 30% sodium methoxide in methanol per kilogram of solution. The pH was checked by means of a glass electrode immersed in a mixture of equal weights of the methanolic solution of butynediol and nickel acetate and of water.

The hydrogenation was carried out in a vertical tube reactor with a height-to-diameter ratio of 40:1. The volume of the reactor was 1 000 units. The tube reactor contained no internal structures and was fed from the bottom; the outlet at the top was connected to a high-pressure separator. The hydrogen inlet was also at the bottom of the reactor. The hydrogen pressure in the tube reactor and separator was 250 bar. The volume of hydrogen leaving the gas side of the high-pressure separator hourly and passing to waste was from 100 units to 1 000 units measured at s.t.p. The feed was preheated to from 180° C. to 190° C. and pumped into the reactor continuously. The heat of hydrogenation was removed by means of an internal coil connected to an external heat exchanger. Cooling can however be accomplished just as well by circulating reaction mixture taken from the end of the reactor through an external heat exchanger. The mean temperature in the reactor was maintained at from 185° C. to 195° C. The rate of input of the solution to be hydrogenated into the reactor was 500 mass units/h.

The rate of output of reaction mixture was 500 mass units/h. That part of the mixture that was not water or methanol contained the following components in the mass fractions stated:

| | |
|---|---|
| 1-butanol | 0.4% |
| hydroxybutyraldehyde | 0.005% |
| 1,4-butanediol | 99% |
| 2-methyl-1,4-butanediol | <0.1% |
| acetals | <0.01% |
| unknowns | 0.1% |
| nonvolatiles | 0.4% |

After the process had been running for 90 d the fresh input of nickel acetate could be reduced to 30% of the original concentration without affecting the hydrogenation. The metallic nickel that began to appear in the output after the reaction had been going on for a few days was filtered off by means of a sintered metal filter candle (Material 14404, fineness 65 microns) interposed between the tube reactor and the high-pressure separator. After another 20 d the output was diverted to a parallel metal filter candle. The first metal filter candle was removed and the metallic nickel collected in it converted back into nickel acetate, which was then employed again for the hydrogenation of butynediol. There was no consumption of catalyst over and above mechanical losses. Magnetic separation can also be used to recover metallic nickel quantitatively from the output mixture.

To remove heat of reaction by direct cooling reaction mixture was taken from the end of the reactor at a rate 25 times the rate of input of feed cooled to a temperature of from 160° C. to 170° C., and returned to the bottom of the reactor. The ratio of the rate of recirculation to the rate of input of fresh feed was always 25:1 on average.

EXAMPLE 2

Granules of nickel-aluminum alloy catalyst (42% nickel, 58% aluminum) of grain size from 2.5 mm to 3.5 mm were treated with 0.5% sodium hydroxide solution as described in German Laid-Open Application No. 20 04 611 until about 25 % of the aluminum was dissolved away.

Methanolic butynediol solution as described in Example 1 was hydrogenated in the reactor described in Example 1. No nickel acetate was used; instead, the reactor was filled with 1,600 mass units of the nickelaluminum catalyst described above. The pH of the feed solution was adjusted to 8.5 by the addition of 3 ml of 30% sodium methoxide in methanol per kilogram of solution.

The methanolic solution of crude butynediol was fed to the bottom of the hydrogenation reactor at the rate of 200 mass units/h. The temperature in the hydrogenation reactor was kept between 205° C. and 315° C. by recirculating reaction mixture at 25 times the rate of input of fresh solution. The hydrogen pressure in the high-pressure separator was 230 bar. The volume of hydrogen leaving the gas side of the high-pressure separator hourly and passing to waste was 50,000 units measured at s.t.p.

The rate of output of reaction was 200 mass units/h. That part of the mixture that was not water or methanol contained the following components in the mass fractions stated:

| | |
|---|---|
| 1-butanol | 0.7% |
| hydroxybutyraldehyde | <0.001% |
| 1,4-butanediol | >98% |
| 2-methyl-1,4-butanediol | 0.3% |
| acetals | 0.3% |
| nonvolatiles | 0.4% |

After the process had been running for 100 d there was no change in the results described.

EXAMPLE 3

A solution of 3-hexyne-2,5-diol in methanol was hydrogenated by the method described in Example 1. The mass fraction of hexynediol was 60%, and the solution also contained enough nickel acetate to make the mass fraction of nickel 0.5%. The solution was fed to the tube reactor at the rate of 300 mass units/h.

That part of the product that was not methanol or water consisted of about 99.5%, 2,5-hexanediol by weight and about 0.2% 2-hexanol, as determined by gas chromotography. The crude product contained less than 0.3% nonvolatiles.

EXAMPLE 4

The methanolic solution described in Example 1 was hydrogenated. The mass fractions in this solution were 47% 2-butyne-1,4-diol, 0.3% water, 50% methanol, 0.15% formaldehyde, and 2.5% other side products or impurities.

The tube reactor described in Example 1 was used for the hydrogenation; it contained no internal structures other than the thermo-elements required for temperature control during the hydrogenation. The reactor was filled with 900 volume units of catalyst whose composition in terms of the oxides was as follows:

| | |
|---|---|
| nickel oxide | 21.5% |
| copper oxide | 7.3% |
| manganese (II/III) oxides | 2% |
| phosphorus pentoxide | 1% |
| sodium oxide | 0.35% |
| silica | ad 100% |

Before the hydrogenation of butynediol the catalyst was activated by passing hydrogen at atmospheric pressure through it for 48 h. the temperature being steadily increased from 180° C. to 325° C.

For the hydrogenation the methanolic butynediol solution was fed to the bottom of the reactor, and flowed upwards. At the top of the reactor the reaction mixture flowed away freely. Thus the hydrogenation was carried out by the ascending-flow method, and there was no appreciable gas space. The hydrogen was also introduced at the bottom of the tube reactor.

The hydrogen pressure in the tube reactor and high-pressure separator was 280 bar. The volume of hydrogen taken hourly from the gas side of the high-pressure separator and passing to waste was from 100 units to 1,000 units at s.t.p. The feed was preheated to a temperature of 50° C. and pumped into the reactor continuously. The heat of hydrogenation set free was removed by external cooling and by recirculating reaction mixture through an external heat exchanger at the rate of 5,000 volume units/h. The mean temperature in the reactor was maintained at from 120° C. to 130° C. The pH of the reaction mixture was 7.8. The rate of input of the solution to be hydrogenated into the catalyst-filled reactor was 300 mass units/h.

The rate of output of reaction mixture was 300 mass units/h. That part of the mixture that was not water or methanol contained the following components in the mass fractions stated:

| | |
|---|---|
| 1-butanol | 0.6% |
| hydroxybutyraldehyde | <0.05% |
| 1,4-butanediol | >98% |
| 2-methyl-1,4-butanediol | <0.05% |
| acetals | <0.01% |
| unknowns | 0.1% |
| nonvolatiles | 0.6% |

Even after the process had been running for six months the catalyst showed no loss of activity whatever.

We claim:

1. A process for the preparation of an alkanediol by catalytic hydrogenation of an alkynediol of from 3 to 8 carbon atoms at high temperatures and pressures which comprises:

hydrogenating a solution of the alkynediol in an alkanol of from 1 to 8 carbon atoms, in which the mass fraction of alkynediol is greater than 5%, of water at most 10%, and of alkanol from 20% to 85%, at temperatures of from 110° C. to 240° C., under pressure greater than 10 bar, and at a pH greater than 6.

2. A process as claimed in claim 1 wherein the hydrogenation is carried out at temperatures in the range 110° C. to 210° C. and pressures of from 10 bar to 250 bar.

3. A process as claimed in claim 1 wherein a catalyst is used whose catalytically active component consists of more than 50% nickel by weight.

4. A process as claimed in claim 1 wherein the catalyst is added to the solution of alkynediol as the nickel salt of an organic acid and hydrogenation is carried out at temperatures in the range of 170° C. to 240° C.

5. A process as claimed in claim 4 wherein the metallic nickel precipitated from the reaction mixture during hydrogenation is separated and again employed for hydrogenation.

6. A process as claimed in claim 1 wherein a methanolic solution of 2-butyne-1,4-diol is hydrogenated in which the mass fractions of the components are from 30% to 70% 2-butyne-1,4-diol, from 0.2% to 5% water, from 30% to 70% methanol, and from 0.2% to 5% impurities that have arisen in the synthesis of 2-butyne-1,4-diol from acetylene and aqueous formaldehyde.

* * * * *